United States Patent
Ishida et al.

(10) Patent No.: US 8,940,327 B2
(45) Date of Patent: Jan. 27, 2015

(54) AGENT FOR ENHANCING ANTI-TUMOR EFFECT COMPRISING OXALIPLATIN LIPOSOME PREPARATION, AND ANTI-TUMOR AGENT COMPRISING THE LIPOSOME PREPARATION

(75) Inventors: Tatsuhiro Ishida, Tokushima (JP); Hiroshi Kiwada, Tokushima (JP)

(73) Assignees: The University of Tokushima, Tokushima-shi, Tokushima (JP); Taiho Pharmaceutical Co. Ltd., Tokyo (JP)

( * ) Notice: Subject to any disclaimer, the term of this patent is extended or adjusted under 35 U.S.C. 154(b) by 625 days.

(21) Appl. No.: 12/864,280

(22) PCT Filed: Jan. 29, 2009

(86) PCT No.: PCT/JP2009/051499
§ 371 (c)(1),
(2), (4) Date: Jul. 23, 2010

(87) PCT Pub. No.: WO2009/096487
PCT Pub. Date: Aug. 6, 2009

(65) Prior Publication Data
US 2010/0330166 A1    Dec. 30, 2010

(30) Foreign Application Priority Data

Jan. 30, 2008  (JP) .................................. 2008-019141
Dec. 1, 2008   (JP) .................................. 2008-306072

(51) Int. Cl.
*A61K 9/127*    (2006.01)
*A61K 31/282*   (2006.01)
(Continued)

(52) U.S. Cl.
CPC ............... *A61K 31/282* (2013.01); *A61K 9/127* (2013.01); *A61K 9/1271* (2013.01);
(Continued)

(58) Field of Classification Search
CPC ........................................................ A61K 9/127
USPC .............................................................. 424/450
See application file for complete search history.

(56) References Cited

U.S. PATENT DOCUMENTS

| 5,525,603 A | 6/1996 | Shirasaka et al. |
| 5,776,488 A | 7/1998 | Mori et al. |

(Continued)

FOREIGN PATENT DOCUMENTS

| JP | 08-169825 | 2/1996 |
| JP | 2002205945 A | 7/2002 |

(Continued)

OTHER PUBLICATIONS

Trosko et al in Mutation Research, 480-481, pp. 219-229, 2001.*

(Continued)

*Primary Examiner* — Gollamudi Kishore
(74) *Attorney, Agent, or Firm* — Rothwell, Figg, Ernst & Manbeck, P.C.

(57) ABSTRACT

An object of the present invention is to further enhance the antitumor effect when oxaliplatin is administered in combination with a combination drug containing tegafur, gimeracil and oteracil potassium. According to the present invention, by using oxaliplatin encapsulated in a liposome preparation, combination therapy of oxaliplatin plus a combination drug containing tegafur, gimeracil and oteracil potassium, is revealed to show remarkably enhanced antitumor effect without increasing side effects.

6 Claims, 5 Drawing Sheets

(51) Int. Cl.

| | | |
|---|---|---|
| *A61K 31/4412* | (2006.01) | |
| *A61K 31/505* | (2006.01) | |
| *A61K 31/513* | (2006.01) | |
| *A61K 31/53* | (2006.01) | |
| *A61K 31/555* | (2006.01) | |

(52) U.S. Cl.
CPC .......... *A61K 9/1272* (2013.01); *A61K 31/4412* (2013.01); *A61K 31/505* (2013.01); *A61K 31/513* (2013.01); *A61K 31/53* (2013.01); *A61K 31/555* (2013.01)
USPC ........................................................ 424/450

(56) References Cited

U.S. PATENT DOCUMENTS

| | | | |
|---|---|---|---|
| 5,945,122 A * | 8/1999 | Abra et al. ............... | 424/450 |
| 6,518,278 B1 | 2/2003 | Oguro et al. | |
| 2003/0224037 A1 | 12/2003 | Eriguchi et al. | |
| 2004/0005365 A1 | 1/2004 | Oguro | |
| 2004/0022842 A1 | 2/2004 | Eriguchi et al. | |
| 2006/0222696 A1 | 10/2006 | Okada et al. | |
| 2006/0239925 A1 | 10/2006 | Wada | |
| 2008/0306073 A1 | 12/2008 | Koizumi et al. | |
| 2009/0053302 A1 | 2/2009 | Boulikas | |

FOREIGN PATENT DOCUMENTS

| | | | |
|---|---|---|---|
| JP | 2004-010481 | | 1/2004 |
| JP | 2006-248978 | | 9/2006 |
| WO | 92/04028 A1 | | 3/1992 |
| WO | 92/21345 A1 | | 12/1992 |
| WO | 95/24201 A1 | | 9/1995 |
| WO | 2005/120480 A1 | | 12/2005 |
| WO | 2006/115155 A1 | | 11/2006 |
| WO | 2007/035783 | * | 3/2007 |
| WO | 2007/099377 A2 | | 9/2007 |

OTHER PUBLICATIONS

Doi et al., "Development of S-1 metronomic chemotherapy combined with l-OHP in nanocarrier; Study to elucidate mechanism of synergistically increased effects", Abstract of The 4th Annual Meeting of the Japan Society of Clinical Oncology, Nippon Chiryo Gakkaishi, Oct. 1, 2008, 43 (2), pp. 385-0S003-2.
Doi et al., "Study on low dose metronomic chemotherapy of S-1 having effect on intratumoral microenviroment affecting kinetics of liposome in tumor", Summary of Presentation Subject @The 23rd Annual Meeting of the Academy of Pharmacetuical Science and Technology, Japan (APSTJ), Journal of Pharmaceutical Science and Technology, Japan, Apr. 30, 2008, 68(SUPPL.), p. 177.
Suzuki et al., "Effective anti-tumor activitiy of oxaliplatin encapsulated in transferrin-PEG-liposome", International Journal of Pharmaceuticals, 346 (2008), pp. 143-150.
Goldberg, et al., "A Randomized Controlled trial of Fluorouracil Plus Leucovorin, Irinotecan, and Oxaliplatin Combinations in Patients with Previously Untreated Metastatic Colorectal Cancer", Journal of Clinical Oncology, vol. 22, No. 1, Jan. 1, 2004, pp. 23-30.
Rothenberg et al., "Superiority of Oxaliplatin and Fluorouracil-Leucovorin Compared with Either Therapy Alone in Patients with Progressive Colorectal Cancer After Irinotecan and Fluorouracil-Leucovorin: Interim Results of a Phase III Trial", Journal of Clinical Oncology, vol. 21, No. 11, Jun. 1, 2003, pp. 2059-2069.
de Gramont et al., "Leucovorin and Fluorouracil with or without Oxaliplatin as First-Line Treatment in Advanced Colorectal Cancer", Journal of Clinical Oncology, vol. 18, No. 16, Aug. 2000, pp. 2938-2947.
Cassidy et al., "Xelox (Capecitabine Plus Oxaliplatin): Active First-Line Therapy for Patients with Metastatic Colorectal Cancer", Journal of Clinical Onclology, vol. 22, No. 11, Jun. 1, 2004, pp. 2084-2091.
Working et al., Pharmacokinetics, Biodistribution and Therapeutic Efficacy of Doxorubicin Encapsulated in Stealth Liposomes (Doxil), Journal of Liposome Research, 4(I), pp. 667-687, (1994).
Maruyama., "Passive targeting with liposomal drug carriers", Drug Delivery System, vol. 14, No. 6, Nov. 1999, pp. 433-447.
Abu-Lila et al., "Oxaliplatin targeting to angiogenic vessels by PEGylated cationic liposomes suppresses the angiogenesis in a dorsal air sac mouse model", Journal of Controlled Release, 134 (2009), pp. 18-25.
Ishida et al., "Improvement of tumor-targeting therapy wit nanocarriers by changing the tumor microenviroment", 6th International Workshop on Drug Delivery Systems for Naonmedicine, Prague (the Czech Republic) Oct. 3-6 (2008).
Hira et al., "Study on combination therapy of fluoropyrimidine anticancer agent and liposomal oxaliplatin (l-OHP): Influence of difference in l-OHP release on effects and toxicity", Department of Pharmacokietics and Biopharmacetucis, Faculty of Pharmaceutical Sciences, The University of Tokushima), Nov. 9, 2008, 1 page.
Doi et al., "S-1 metronomic chemotherapy has effect on intratumoral microenviroment and enhances accumulation of nanocarrier such as liposome in tumor", Department of Pharmacokinetics and Biopharmacettics, Graduate School of Pharmacy, Sep. 20, 2008, 1 page.
Doi et al., "Effect of liposomalization of intravenous anticancer agent on combination therapy of oral and intravenous anticancer agents", 128th Annual Meeting of the Pharmaceutical Society of Japan, Mar. 26, 2008.
Ishida et al., "Improvement of tumor-targeting therapy with nanocarriers by changing the tumor microenvironment", 11th Liposome Research Days Conference, Yokohama (Japan), Jul. 19-22, 2008.
Doi et al., "Metronomic dosing of oral anticancer agent affects microenvironment in solid tumor, resulting in enhanced intratumoral accumulation and distribution of nanocarrier", 11th Liposome Research Days Conference, Yokohama (Japan), Jul. 19-22, 2008.
Yusuke Tsuchii et al., S-1 Metronomic Chemotherapy to Oxaliplatin Fu'nyu Nano Carrier Heiyo Ryoho no Kaihatsu : Sojoteki Koka Zokyo Kiko no Kaimei ni Kansuru Kenkyu, Nippon Chiryo Gakkaishi, Oct. 1, 2008, 43 (2) , p. 385, OS003-2.
Yusuke Tsuchii et al., "S-1 o Mochiita Low Dose Metronomic Chemotherapy ni yotte Shojiru Shuyonai Bisho Kankyo no Henka ga Ataeru Liposome no Shuyonai Dotai Henka ni Kansuru Kento", Journal of Pharmaceutical Science and Technology, Japan, Apr. 30, 2008, 68 (Suppl.), p. 177.
Suzuki, R. et al. 'Effective Anti-Tumor Activity of Oxaliplatin Encapsulated in Transferrin-peg-Liposome.' Int. J. Pharm., (Jan. 4, 2008) 346 (1-2) p. 143-150, full text.

* cited by examiner figure1 figure2 figure3 figure4 figure5 figure6 figure 7 figure 8 figure9 figure10

AGENT FOR ENHANCING ANTI-TUMOR EFFECT COMPRISING OXALIPLATIN LIPOSOME PREPARATION, AND ANTI-TUMOR AGENT COMPRISING THE LIPOSOME PREPARATION

CROSS REFERENCE TO RELATED APPLICATION

This application is a 35 U.S.C. 371 National Phase Entry Application from PCT/JP2009/051499, filed Jan. 29, 2009, which claims the benefit of Japanese Patent Application Nos. 2008-19141 filed on Jan. 30, 2008 and 2008-306072 filed on Dec. 1, 2008, the disclosures of which are incorporated herein in their entirety by reference.

TECHNICAL FIELD

The present invention relates to an agent for enhancing antitumor effect comprising oxaliplatin lipolome preparation. The present invention also relates to an antitumor agent comprising the liposome preparation.

BACKGROUND ART

Heretofore, many anticancer agents have been developed and used in the medical field. For example, tegafur is a anticancer agent that is activated in vivo and gradually releases the active form, i.e., 5-fluorouracil (hereinafter referred to as "5-FU"), thereby lessening the toxicity or side effects presented by 5-FU. A combination drug containing the three pharmaceutical agents of tegafur, gimeracil and oteracil potassium (trade name: TS-1, molar ratio of tegafur/gimeracil/oteracil potassium=1:0.4:1, manufactured by Taiho Pharmaceutical Co., Ltd., hereunder this combination drug is referred to as TS-1) has a further stronger antitumor effect because gimeracil inhibits the degradation of 5-FU. In this preparation, since oteracil potassium specifically inhibits the onset of gastrointestinal toxicity that is likely to be accompanied by the potentiation of the antitumor effect attained by the two pharmaceutical agents, i.e., tegafur and gimeracil, the therapeutic effect being thereby improved. TS-1 therefore contributes to the treatment of various malignant tumors (Patent Document 1).

However, therapeutic agents and methods which have stronger therapeutic effects enough to prolong the survival of cancer patients are still deemed necessary. Administering combination chemotherapy of various agents (combination therapy), whose mechanism of action of antitumor effect and/or side effect are differ from one another, is attempted to improve therapeutic effect and some combination therapies actually contribute to improvement of cancer treatment (see, for example, Patent Documents 2, 3 and 4). For example, oxaliplatin exhibits a low antitumor effect when used alone, and is therefore used in combination with other pharmaceutical agents. Combination therapy using 5-fluorouracil and folinate (hereunder, folinate is referred to as LV) (FOLFOX) are commonly used worldwide (see, for example, Non-Patent Documents 1, 2, and 3). However, the application of FOL-FOX is complicated and extended periods of infusional 5-FU reduce patient's QOL because of the physical restraint that accompanies continuous intravenous infusion, moreover, high medical costs. Therefore developments of better combination therapies using oxaliplatin are being made all over the world. As an example, a combination therapy using oxaliplatin and capecitabine (trade name: Xeloda), which is an oral fluorinated pyrimidine, (XELOX) is reported to provide an antitumor effect almost identical to FOLFOX (see, for example, Non-Patent Document 4). As a novel approach has been indicated that TS-1 and oxaliplatin provides remarkable antitumor effect, as in this case, that has superior therapeutic efficacy to the case oxaliplatin in combination with capecitabin (Patent Document 5). However, a stronger therapeutic effect is still required.

As described above, oxaliplatin exhibits a low antitumor effect when used singly and one of the reason is a low accumulation of the agents in tumor tissue. When an antitumor agent is administered, it may quickly disappear from the blood circulation or be distributed to healthy organs; therefore, the antitumor agent does not accumulate in the tumor tissue effectively. Accordingly, many antitumor agents cannot always exhibit a sufficient antitumor activity, and they often undesirably affect normal tissues (side effects), causing critical toxicity. Enhancing efficacy of antitumor agents is an important object in current cancer chemotherapies, and development of drug delivery system (DDS) by which drugs can effectively accumulate in tumor is strongly desired.

Liposome is a closed vesicle comprising phospholipids, which are derived from biological material, as a main component. So liposomes exhibits low toxicity and antigenicity when administered to a living body. Furthermore, some reports indicate that encapsulation of drugs in liposome enables to control their stability in blood and biodistribution, resulting in improved delivery efficiency of their payloads to the targeted tissues (Patent Documents 6, 7 and 8 and Non-Patent Document 5). It is also known that vesicles such as liposome which has a particle size of 100 to 200 nm effectively accumulate in tumor, because angiogenic vessels present in tumor show relatively high permeability compared with blood vessels in healthy tissue (Non-Patent Document 6).

Patent Document 1: Japanese Patent No. 2614164
Patent Document 2: Japanese Patent No. 2557303
Patent Document 3: Japanese Unexamined Patent Publication No. 1996-169825
Patent Document 4: Japanese Unexamined Patent Publication No. 2002-205945
Patent Document 5: WO2005/120480
Patent Document 6: WO95/24201
Patent Document 7: Japanese Patent No. 3415131
Patent Document 8: Japanese Unexamined Patent Publication No. 2006-248978
Non-Patent Document 1: Journal of Clinical Oncology, Vol. 22, 23-30, 2004
Non-Patent Document 2: Journal of Clinical Oncology, Vol. 21, 2059-2069, 2003
Non-Patent Document 3: Journal of Clinical Oncology, Vol. 18, 2938-2947, 2000
Non-Patent Document 4: Journal of Clinical Oncology, Vol. 22, 2084-2091, 2004
Non-Patent Document 5: Journal of Liposome Research, Vol. 4, 667-687, 1994
Non-Patent Document 6: Drug Delivery System, Vol. 14, 433-447, 1999

DISCLOSURE OF THE INVENTION

Problem to be Solved by the Invention

A primary object of the invention is to enhance the antitumor effect of a combination drug comprising tegafur, gimeracil and oteracil potassium without increasing toxicity. Another object of the present invention is to provide an antitumor agent and kit exhibit a higher antitumor effect than an antitumor agent comprising tegafur, gimeracil and oteracil potassium in combination with oxaliplatin.

Means for Solving the Problem

In view of the current state of the art described above, the inventors conducted extensive research to develop a method for treating cancer that strongly contributes to prolonging the survival of patients. As a result, l-OHP-containing liposome, which is a liposome preparation stably encapsulating a platinum complex, i.e., cis-oxalate(1R,2R-diaminocyclohexane) platinum(II) (generic name: oxaliplatin, trade name: Eloxatin or Elplat, hereinafter referred to as l-OHP) and has suitably adjusted particle size, was developed. The antitumor effects of a combination drug comprising tegafur, gimeracil, and oteracil potassium, can be remarkably improved by combining with l-OHP-containing liposomes, without increasing side effects. The present invention has been accomplished based on these novel findings.

In particular, the present invention provides an antitumor effect potentiator, antitumor agent, antitumor agent kit, etc., as described below.

Item 1. An antitumor agent combinedly comprising a liposome preparation encapsulating oxaliplatin in a liposome, and a combination drug containing tegafur, gimeracil and oteracil potassium.

Item 2. The antitumor agent according to Item 1, wherein at least one lipid component that constitutes the liposome is phospholipid.

Item 3. The antitumor agent according to Item 2, wherein the membrane surface of liposome is modified with polyethylene glycol, polyglycerin or cationic lipid.

Item 4. The antitumor agent according to any one of Items 1 to 3, wherein the oxaliplatin is used in a proportion of 0.1 to 5 mol per 1 mol of tegafur.

Item 5. The antitumor agent according to Item 1, wherein the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

Item 6. The antitumor agent according to Item 1, wherein the antitumor agent is formed as a kit that comprises a liposome preparation containing oxaliplatin, and a combination drug containing tegafur, gimeracil and oteracil potassium.

Item 7. The antitumor agent according to Item 1, wherein the liposome preparation is administered intravenously, intraperitoneally, intramuscularly or subcutaneously, and the combination drug containing tegafur, gimeracil and oteracil potassium is administered orally.

Item 8. An antitumor effect potentiator, which is a liposome preparation containing an effective amount of oxaliplatin in a liposome, for enhancing antitumor activity of a therapeutically effective amount of a combination drug containing tegafur, gimeracil and oteracil potassium.

Item 9. The antitumor effect potentiator according to Item 8, wherein at least one lipid component that constitutes the liposome is phospholipid.

Item 10. The antitumor effect potentiator according to Item 9, wherein the membrane surface of liposome is modified with polyethylene glycol, polyglycerin or cationic lipid.

Item 11. The antitumor effect potentiator according to any one of Items 8 to 10, wherein the oxaliplatin is used in a proportion of 0.1 to 5 mol per 1 mol of tegafur.

Item 12. The antitumor effect potentiator according to Item 8, wherein the gimeracil is used in a proportion of 0.1 to 5 mol per 1 mol of tegafur, and the oteracil potassium is used in a proportion of 0.1 to 5 mol per 1 mol of tegafur, in the combination drug containing tegafur, gimeracil and oteracil potassium.

Item 13. Use of a liposome preparation obtainable by encapsulating oxaliplatin in a liposome, and a combination drug containing tegafur, gimeracil and oteracil potassium for producing an antitumor agent.

Item 14. Use of a liposome preparation obtainable by encapsulating oxaliplatin in a liposome for producing an antitumor effect potentiator.

Item 15. A therapeutic method for cancer characterized by administering effective amounts of a liposome preparation encapsulating oxaliplatin, and a combination drug containing tegafur, gimeracil and oteracil potassium to a cancer patient.

Effect of the Invention

The antitumor effect potentiator of the present invention can enhance the antitumor effect of a combination drug containing the three pharmaceutical agents of tegafur, gimeracil, and oteracil potassium, which is a known antitumor agent, without increasing toxicity, compared to the case where l-OHP is used in combination. Accordingly, the antitumor agent and antitumor agent kit of the present invention achieve a remarkable effect, i.e.; exhibiting an antitumor effect that is superior to a combination therapy in which a combination drug containing the three pharmaceutical agents of tegafur, gimeracil and oteracil potassium is used in combination with l-OHP, while not increasing a level of toxicity. The present invention is expected to be applied to a therapeutic method for further prolonging the survival of cancer patients.

BEST MODE FOR CARRYING OUT THE INVENTION (1) Antitumor Effect Potentiator

The present invention provides an antitumor effect potentiator for enhancing the antitumor activity of a therapeutically effective amount of a combination drug containing therapeutically effective amounts of tegafur, gimeracil and oteracil potassium. The antitumor effect potentiator is prepared as a liposome preparation obtainable by encapsulating an therapeutically effective amount of oxaliplatin (l-OHP) for improving the antitumor effect in a liposome that is composed of at least one lipid component.

(1-1) Liposome Preparation l-OHP l-OHP is a known compound of platinum complex. l-OHP binds to DNA in cancer cells and then induces interruption of DNA function and DNA strand breakage, resulting that this agent exert cytotoxicity against cancer cells. l-OHP can be produced according to known methods, for example, the method disclosed in Japanese Examined Patent Publication No. 1985-41077.

Liposome

The liposome used in the liposome preparation of the present invention is a vesicle that is formed by dispersing phospholipid, which is a main component of cell membrane, in water and has an internal aqueous phase surrounded by lipid membranes. Liposomes can be classified into three categories depending on the particle size and the number of lipid layer, i.e., a multilamellar vesicle: MLV, a large unilamellar vesicle: LUV, and a small unilamellar vesicle: SUV. Any type of liposome can be used in the present invention. The liposome used in the present invention is required to have a stable form before and after administration into the body. Examples of phospholipids that form liposomes include hydrogenated purified egg yolk phosphatidylcholine (phase transition temperature of 50° C., hereunder referred to as HEPC), hydrogenated refined soybean phosphatidylcholine (phase transition temperature of about 55° C., hereunder referred to as HSPC), dipalmitoylphosphatidylcholine (phase transition temperature of about 41° C., hereunder referred to as DPPC), distearoylphosphatidylcholine (phase transition temperature of about 58° C., hereunder referred to as DSPC) and 1-palmitoyl-2-oleoylphosphatidylcholine (phase transition temperature of −3° C. Among these, HEPC, HSPC, DPPC, and DSPC are preferable.

In this specification, hydrogenated purified egg yolk phosphatidylcholine means that obtained by hydrogenation of phosphatidylcholine derived from egg yolk. One example of hydrogenated purified egg yolk phosphatidylcholine used in a preferable embodiment comprises, as a main component, phosphatidylcholine of which acyl moiety is a $C_{16-18}$ acyl group derived from saturated straight-chain fatty acid. In the present invention, the hydrogenated purified egg yolk phosphatidylcholine is obtained by purifying hydrogenated egg yolk phosphatidylcholine; and, for example, those having a purity of not less than 80%, and preferably those having a purity of not less than 90% are usable.

In this specification, hydrogenated soybean phosphatidylcholine means that obtained by hydrogenation of phosphatidylcholine derived from soybean. One example of hydrogenated soybean phosphatidylcholine used in a preferable embodiment comprises, as a main component, phosphatidylcholine of which acyl moiety is a $C_{16-18}$ acyl group derived from a saturated straight-chain fatty acid. In the present invention, hydrogenated refined soybean phosphatidylcholine is obtained by refining hydrogenated soybean phosphatidylcholine; and, for example, those having purity of not less than 80%, and preferably those having purity of not less than 90% are usable.

These phospholipids may be used singly or in a combination of two or more. By using phospholipids having different phase transition temperatures, the fluidity of the bimolecular lipid membrane of liposome can be changed. This allows selection of the most suitable phospholipid in view of the encapsulation rate, stability in a pharmaceutical preparation, in vivo dynamics after administration and the like.

In addition to these phospholipids, the liposome used in the present invention is preferably mixed with a stabilizer, such as a cholesterol that is reported to improve the stability of the liposome or its derivative. Furthermore, stability in blood, tissue distribution, translatability to tumor tissue and the like of the liposome can be further improved by modifying the liposome membrane surface, if necessary, with a ligand selected from polyethylene glycol, polyglycerin or a like hydrophilic high polymer material; a lipid that contains an amino group, amidino group, guadinino group or a like basic functional group (hereunder referred to as a cationized lipid); or a peptide, lectin, antibody, saccharide, glycoprotein, glycolipid or the like.

In the present invention, the "polyethylene glycol" includes not only unsubstituted polyethylene glycols but also derivatives of which oleophilic (hydrophobic) side chain was subjected to a covalent bond. Specific examples of oleophilic side chains include alkyl chain, phospholipid, and cholesterol. Various polyethylene glycol derivatives that are ordinarily used to improve the stability of liposome can be used in the present invention. Similarly, the "polyglycerin" of the present invention includes not only unsubstituted polyglycerin but also derivatives of which oleophilic (hydrophobic) side chain was subjected to a covalent bond. Specific examples of the oleophilic side chain include an alkyl chain, phospholipid, and cholesterol. Various polyglycerin derivatives that are ordinarily used to improve the stability of liposome can be used in the present invention. Furthermore, glycerol, glucose, sodium chloride or the like may be added as an isotonizing agent. Furthermore, parabens, chlorobutanol, benzyl alcohol, propylene glycol and like preservatives may also be added.

Liposome Preparation

The liposome preparation of the present invention can be produced by a known method. Examples of known methods for producing a liposome preparation include a reverse phase evaporation method (Proc. Natl. Acad. Sci. USA, Vol. 75, 4194, 1978, WO97/48398), freeze-thawing method (Arch. Biochem. Biophys, Vol. 212, 186, 1981), pH-gradient method (Biochem. Biophys. Acta, Vol. 816, 294, 1985, Japanese Unexamined Patent Publication No. 1995-165560) and the like.

Among these methods, when the reverse phase evaporation method is employed, the liposome preparation of the present invention is produced by the following process. For example, a lipid component is dissolved in chloroform, ether, ethanol or a like solvent, and the resulting dissolution is placed in a pear shaped flask. The solvent is removed by evaporation under a reduced pressure, forming a lipid thin film. Subsequently, a mixed liquid containing chloroform and diethyl ether in a ratio of chloroform/diethyl ether=½ is added to dissolve the thin film. An aqueous solution containing the active agent is added thereto, and the mixture is sonicated at 25° C. for 15 minutes to obtain an emulsion. The organic phase of resulting emulsion is removed to transfer a w/o emulsion to an o/w emulsion by evaporation in a rotary evaporator for one hour, while being vortexed. Liposome is thereby formed and the pharmaceutical agent is encapsulated in the liposome. The process described above allows the pharmaceutical agent to be encapsulated in liposome.

It was reported that the particle size of the liposome strongly affects biodistribution and tumor accumulation of their payload (Biol. Pharm. Bull., Vol. 17, 935, 1994). In the present invention, particle sizing is preferably conducted in order to obtain a desirable and uniformly sized liposome containing a pharmaceutical agent therein. For example, by conducting a supersonic treatment using a biodisruptor (manufactured by Nippon Seiki Co., Ltd., etc.) or a high pressure emulsification using a nanomizer (manufactured by Yoshida Kikai Co., Ltd.), etc., the particle size of the liposome can be adjusted to have an average particle diameter of about 100 to 200 nm. Alternatively, by subjecting the liposome-containing solution to sizing under nitrogen pressure using various polycarbonate membrane filters (0.4 µm, 0.2 µm, 0.1 µm, and 0.08 µm), the particle size of the liposome can be adjusted to have an average particle diameter of about 100 to 300 nm.

In the present invention, the term "average particle diameter" means an average particle diameter measured by a light scattering method using a NICOMP 370 HPL submicron particle analyzer (manufactured by Particle Sizing System, Inc.).

Stability in blood, tissue distribution, and tumor localization of the liposome can be further improved by modifying the membrane surface of liposome, if necessary, with polyethylene glycol, polyglycerin, cationized lipid, or a ligand such as peptide, lectin, antibody, saccharide, glycoprotein, or glycolipid.

The liposome preparation of the present invention may also be produced by a method of Patent Document 7 (Japanese Patent No. 3415131) or Patent Document 8 (Japanese Unexamined Patent Publication No. 2006-248978), which disclose oxaliplatin (l-OHP) liposome preparations.

In a preferable embodiment, the liposome preparation of the present invention is produced using a solution that is obtained by dissolving l-OHP in a 1 to 10% glucose solution in such a manner that the concentration of l-OHP becomes 1 to 20 mg/mL, as the l-OHP solution.

The l-OHP-containing liposome preparation thus obtained is subjected to, if necessary, ultracentrifugation, gel filtration, ultrafiltration, and dialysis. These treatments may be suitably conducted singly or in combination, pharmaceutical agents that were not encapsulated in the liposome are thereby removed.

The l-OHP-containing liposome preparation obtained by the above-mentioned method may be used directly. However, in view of the storage time, conditions, etc., the l-OHP-containing liposome preparation may be freeze-dried after adding excipients such as mannitol, trehalose, lactose, glycine. Alternatively, the l-OHP-containing liposome preparation may be cryopreserved after adding cryopreservation agents such as glycerol.

In a preferable embodiment, the l-OHP liposome preparation contains oxaliplatin in an amount of 1 to 50 µg/mg lipid, and preferably 5 to 40 µg/mg lipid.

The l-OHP-containing liposome preparation of the present invention has an average particle diameter of preferably 50 to 300 nm, and more preferably 80 to 200 nm.

The l-OHP-containing liposome preparation is generally suspended or diluted with a physiologically acceptable aqueous solution, and then used as an injectable preparation (intravenously, intraperitoneally, intramuscularly, or subcutaneously administered preparation); however, the l-OHP-containing liposome preparation may also be used as an oral preparation, collunarium, inhalant, suppository, percutaneously absorbed preparation, permucosally absorbed preparation, etc. In this case, the l-OHP-containing liposome preparation is formed into a preparation composition using appropriate carriers by following an ordinary method. Carriers usable herein are those that are commonly used in conventional pharmaceutical preparations. Specific examples thereof include excipients, binders, disintegrators, lubricants, coloring agents, taste enhancers, flavor enhancers, surfactants, etc.

Examples of the combination drug containing tegafur, gimeracil and oteracil potassium, of which antitumor effect can be enhanced by the antitumor effect potentiator of the present invention, are described below.

(1-2) Combination drug Containing Tegafur, Gimeracil and Oteracil Potassium

Tegafur

Tegafur (generic name, chemical name: 5-fluoro-1-(2-tetrahydrofuryl)-2,4-(1H, 3H)-pyrimidinedione) is a known compound that is activated in vivo to release 5-FU, i.e., an active form for exerting an antitumor activity. Tegafur can be produced according to known methods, for example, the method disclosed in Japanese Examined Patent Publication No. 1974-10510.

Gimeracil

Gimeracil (generic name, chemical name: 2,4-dihydroxy-5-chloropyridine) is also a known compound, and it does not exhibit any antitumor activity by itself. However, it can inhibit metabolic inactivation of 5-FU in vivo, resulting in increasing antitumor effect of 5-FU.

Oteracil Potassium

Oteracil potassium (generic name, chemical name: monopotassium 1,2,3,4-tetrahydro-2,4-dioxo-1,3,5-triazine-6-carboxylate) is also a known compound. Although it does not exhibit any antitumor activity by itself, it mostly remains in the gastrointestinal tract and inhibits the activation of 5-FU therein, thereby preventing gastrointestinal tract disorders caused by 5-FU.

With respect to the combination drug containing three ingredients, i.e., tegafur, gimeracil, and oteracil potassium, as active ingredients, the proportion of each active ingredient may be within the ranges described in connection with a known pharmaceutical agent such as, for example, that disclosed in Patent Publication No. 2614164. The proportion is usually such that, per 1 mol of tegafur, gimeracil is used in a proportion of about 0.1 to 5 mol and preferably about 0.2 to 1.5 mol, and oteracil potassium is used in a proportion of about 0.1 to 5 mol and preferably about 0.2 to 2 mol. A particularly preferable proportion of the three ingredients is tegafur:gimeracil:oteracil potassium=1:0.4:1 in molar ratio.

The combination drug containing tegafur, gimeracil, and oteracil potassium as active ingredients may be prepared in a pharmaceutical form comprising two or more pharmaceutical agents each of which contains one of the active ingredients, or each of which contains the active ingredients in any combination, or in a pharmaceutical form comprising a single pharmaceutical agent containing all of the active ingredients. In either case, such combination drugs are prepared as pharmaceutical compositions according to ordinary methods using suitable pharmaceutical carriers. Carriers usable herein are those that are commonly used in conventional pharmaceutical preparations, for example, excipients, binders, disintegrators, lubricants, colorants, taste enhancers, flavor enhancers, surfactants, etc.

When a combination drug in a pharmaceutical form comprising two or more pharmaceutical agents is used, each pharmaceutical agent may be administered concurrently, or one pharmaceutical agent may be administered at any time before or after the administration of the other pharmaceutical agent(s). Preferably, all of the pharmaceutical agents are administered concurrently, or one pharmaceutical agent is administered within 4 hours, and more preferably within 2 hours, before or after the administration of the other pharmaceutical agent(s).

(1-3) Administration Method

The aforementioned antitumor effect potentiator (i.e., l-OHP-containing liposome preparation) may be administered separately or concurrently with a combination drug that contains three ingredients, i.e., tegafur, gimeracil, and oteracil potassium, as active ingredients, that has been prepared in a unit dosage form. More specifically, the antitumor effect potentiator of the present invention can be administered concurrently or at any time before or after the administration of the antitumor agents containing the three ingredients, i.e., tegafur, gimeracil, and oteracil potassium, as active ingredients. Preferably, the antitumor effect potentiator is administered concurrently or within 4 hours before or after the administration of the antitumor preparation, and preferably within 2 hours before or after the administration of the antitumor preparation. When continuously administered, the administration frequency and intervals of administration of the antitumor agent and antitumor effect potentiator should be suitably selected.

When the l-OHP-containing liposome preparation is administered concurrently or separately from the antitumor preparation containing the three active ingredients of tegafur, gimeracil and oteracil potassium, the antitumor effect potentiator is preferably administered in an amount such that the amount of l-OHP, per 1 mol of tegafur, is within the range of about 0.1 to 5 mol, preferably about 0.1 to 3 mol, and more preferably about 0.2 to 2 mol.

(2) Antitumor Agent

The present invention provides an antitumor agent comprising a combination drug containing the three active ingredients of tegafur, gimeracil and oteracil potassium, in combination with antitumor effect potentiator (the l-OHP-containing liposome preparation). The antitumor agent may be in a pharmaceutical preparation comprising a plurality of pharmaceutical agents each of which contains one of the aforementioned four ingredients, i.e., the three ingredients described above and l-OHP-containing liposome, or each of which contains such ingredients in any combination, or in a pharmaceutical form comprising a single pharmaceutical agent containing all of the ingredients. More specifically, the antitumor agent of the present invention may be formed into a single dosage form containing all of the aforementioned four ingredients, or a multiple dosage form comprising a pharmaceutical agent containing 1 to 3 ingredients and one or more pharmaceutical agents containing the rest of the ingredients. A particularly preferable example is a 2-part preparation in which a pharmaceutical agent containing the three ingredients of tegafur, gimeracil, and oteracil potassium, as active ingredients, and a pharmaceutical agent containing l-OHP encapsulated in a liposome preparation are present as separate formulation.

With respect to the antitumor preparation, the proportion of the ingredients is not limited, irrespective of being composed of a single pharmaceutical agent or multiple pharmaceutical agents. Usually, per 1 mol of tegafur, gimeracil is used in a proportion of about 0.1 to 5 mol and preferably about 0.2 to 1.5 mol; oteracil potassium is used in a proportion of about 0.1 to 5 mol and preferably about 0.2 to 2 mol; and l-OHP is used in a proportion of about 0.1 to 5 mol, preferably about 0.1 to 3 mol and more preferably about 0.2 to about 2 mol. In particular, a preferable molar ratio of the ingredients is tegafur:gimeracil:oteracil potassium:l-OHP=about 1:0.4:1:0.1 to 5, more preferably about 1:0.4:1:0.1 to 3, and particularly preferably about 1:0.4:1:0.2 to 2. When the antitumor preparation is a 2 dosage form in which a pharmaceutical agent containing the three ingredients of tegafur, gimeracil, and oteracil potassium as active ingredients, and l-OHP-containing liposome are present as separate formulations as described above, the antitumor agents preferably contains a combination drug containing tegafur, gimeracil, and oteracil potassium in a molar ratio of 1:0.4:1, and a pharmaceutical preparation containing, per 1 mol of tegafur, l-OHP in a proportion of about 0.1 to 5 mol, preferably about 0.1 to 3 mol, and more preferably about 0.2 to about 2 mol.

The active ingredients may be prepared as pharmaceutical compositions according to standard methods using suitable pharmaceutical carriers. Carriers usable herein are those that are commonly used in conventional pharmaceutical preparations, for example, excipients, binders, disintegrators, lubricants, colorants, taste enhancers, flavor enhancers, surfactants, etc.

When an antitumor preparation which has multiple dosage form and comprises two or more pharmaceutical agents as described above is used, each pharmaceutical agent may be administered concurrently, or each pharmaceutical agent may be administered at any time before or after the administration of the other pharmaceutical agent(s). Preferably, all of the pharmaceutical agents are administered concurrently, or one pharmaceutical agent is administered within 4 hours, and more preferably within 2 hours, before or after the administration of the other pharmaceutical agents.

(3) Kit

The present invention provides a kit comprising the l-OHP-containing liposome preparation with a combination drug containing tegafur, gimeracil and oteracil potassium. More specifically, the present invention provides a kit for mammalian cancer treatment comprising:

(a) an antitumor composition that contains a therapeutically effective amount of tegafur, an effective amount of gimeracil for potentiating an antitumor effect, and an effective amount of oteracil potassium for inhibiting side effects, and (b) a liposome preparation encapsulating an effective amount of l-OHP for potentiating an antitumor effect.

The compositions contained in such a kit may be in any known pharmaceutical form. The compositions are usually placed in any commonly used containers according to their pharmaceutical form.

The kit is used for treating mammal cancer and comprises:
(i) tegafur in a therapeutically effective amount,
(ii) gimeracil in an amount effective for potentiating an antitumor effect,
(iii) oteracil potassium in an amount effective for inhibiting side effects; these all being part of an antitumor composition, and
(iv) liposome that contains l-OHP in an amount effective for potentiating an antitumor effect.

The kit comprises at least 2 containers for these ingredients, and tegafur and l-OHP are packaged in separate containers. The aforementioned ingredients (i) to (iv) are preferably in a pharmaceutical form prepared in combination with pharmaceutically acceptable carriers. With respect to the aforementioned kit, insofar as ingredients (i) and (iv) are stored in separate containers, ingredients (ii) and (iii) may be independently stored in containers that are separate from those in which the aforementioned two ingredients are stored, or ingredients (ii) and (iii) may be independently mixed with ingredient (i) or (iv) for storing in the same container. A kit in which a pharmaceutical agent containing ingredients (i) to (iii) is stored in one container and a pharmaceutical agent containing ingredient (iv) is stored in another container is preferable.

Usable unit dosage forms of the antitumor agent of the present invention for treating mammals including human beings suffering from malignant tumors are not limited, and can be suitably selected according to the purpose of the treatment. Specific examples are injections, suppositories, ophthalmic solutions, ointments, aerosols, and like parenteral forms; tablets, coated tablets, powders, granules, capsules, fluids, pills, suspensions, emulsions, and like oral forms. The antitumor agent can be produced in such dosage forms according to methods commonly known in this technical field.

The amounts of tegafur, gimeracil, oteracil potassium, and l-OHP, which are active ingredients of the antitumor preparation of the present invention, vary according to the dosage form, route of administration, dosing schedule, etc., and are not limited, and hence can be suitably selected. It is usually preferable that the proportion of the active ingredients accounts for about 1 to about 70 wt. % of the pharmaceutical preparation.

Methods for administration of the pharmaceutical preparation of the present invention are not limited and can be determined according to the form thereof, the age, sex, and condition of the patient, and other factors; and hence it may be administered enterally, orally, rectally, intraorally, intraarterially, intravenously, transdermally, or in a like manner. For example, tablets, pills, solutions, suspensions, emulsions, granules, capsules, and the like are administered orally; injections are administered intraarterially or intravenously; suppositories are administered intrarectally; and ointments are applied to the skin, the mucous membrane in the mouth, etc. With respect to the pharmaceutical preparation of the present invention, it is possible that the pharmaceutical agent containing tegafur, gimeracil, and oteracil potassium is orally administered while the l-OHP pharmaceutical agent encapsulated in liposome is intravenously administered.

The dosage of each active ingredient in the present invention can be suitably selected according to the application, the age and sex of the patient, the degree of the disease, and other factors. The antitumor effect potentiator and the antitumor preparation of the present invention can be administered in 1 to 4 doses per day.

In oral administration, the pharmaceutical preparation of the present invention is preferably given in an amount using the following ranges as a standard: the amount of tegafur is about 0.1 to 100 mg/kg/day, preferably about 0.2 to 40 mg/kg/day, and more preferably about 0.5 to 20 mg/kg/day; the amount of gimeracil is about 0.02 to 30 mg/kg/day, preferably about 0.05 to 12 mg/kg/day, and more preferably about 0.1 to 6 mg/kg/day; the amount of oteracil potassium is about 0.1 to 100 mg/kg/day, preferably about 0.2 to 40 mg/kg/day, and more preferably about 0.5 to 20 mg/kg/day; and the amount of l-OHP is about 0.08 to 200 mg/kg/day, preferably about 0.15 to 80 mg/kg/day, and more preferably about 0.4 to 40 mg/kg/day.

When in the form of an injection, the pharmaceutical preparation, which may be diluted with an aqueous glucose solution if necessary, can be gradually administered to an adult over 5 minutes or longer, usually in an amount corresponding to about 0.1 to 100 mg/kg/day of tegafur and about 0.08 to 200 mg/kg/day of l-OHP.

When in the form of a suppository, the pharmaceutical preparation of the invention is administered once or twice a day to an adult, at an interval of 6 to 12 hours, usually in an amount corresponding to about 0.1 to 100 mg/kg/day of tegafur and about 0.08 to 200 mg/kg/day of l-OHP by inserting it into the rectum.

The types of malignant tumors treatable by the administration of the pharmaceutical preparation of the present invention are not limited, insofar as the active form, i.e., 5-FU, is reactive thereto; for example, lung cancer, gastric cancer, colon cancer, rectal cancer, esophageal cancer, breast cancer, head and neck cancer, liver cancer, gallbladder/biliary cancer, pancreatic cancer, uterine cancer, cervical cancer, ovarian cancer, renal cancer, vesical cancer, prostatic cancer, pharyngeal cancer, brain tumor, leukemia, melanoma, a malignant lymphoma, etc. In particular, a remarkable effect on colon cancer, rectal cancer, gastric cancer, esophageal cancer, breast carcinoma, and head and neck cancer can be expected from the pharmaceutical preparation of the present invention. Furthermore, a remarkable effect on typical drug-resistant tumors and tumors that are developing drug resistance can also be expected.

EXAMPLES

Examples and Test Examples are given below to illustrate the invention in more detail, but the scope of the invention is not limited by these Examples and Test Examples.

Example 1

DPPC (L-α-Dipalmitoyl Phosphatidylcholine, Coatsome MC-6060, manufactured by NOF Corporation), cholesterol (special grade, manufactured by Wako Pure Chemical Industries, Ltd.), and mPEG$_{2000}$-DSPE (1,2-distearoyl-sn-glycero-3-phosphoethanolamine-n-[methoxy(polyethylene glycol)-2000], Sunbright DSPE-020CN, manufactured by NOF Corporation) were dissolved in chloroform to obtain respective concentrations of 20 mM, 50 mM, and 5 mM. Subsequently, 5 mL of 20 mM DPPC solution, 0.5 mL of 50 mM cholesterol solution, and 1 mL of 5 mM mPEG$_{2000}$-DSPE solution were placed in a pear shaped flask. While reducing the pressure using an evaporator, chloroform was removed to form a lipid thin film on the bottom of the pear shaped flask. The lipid thin films were dissolved in 6 mL of chloroform/diethyl ether (1:2 v/v). l-OHP was dissolved in a 5% glucose solution so that the concentration of l-OHP became 8 mg/mL. l-OHP solution thus prepared (2 mL) was added to the lipid solution and then mixed. The resulting mixture was sonicated at 25° C. for 15 minutes to form w/o emulsion, and the organic phase was removed under a reduced pressure using an evaporator while being vortexed; the l-OHP was thereby encapsulated in liposome. A supersonic treatment for particle sizing was conducted using a biodisruptor (Nippon Seiki Co., Ltd.) so that the average particle diameter of the liposome containing a pharmaceutical agent therein became about slightly less than 200 nm. In order to remove pharmaceutical agents that were not encapsulated in liposome, dialysis was conducted at 4° C. for 2 hours using a dialysis cassette (Slide-A-Lyzer Dialysis Cassettes, 10000 MWCO, manufactured by Thermo Scientific Inc.) and a 5% glucose solution as an external solution while stirring with a magnetic stirrer. After exchanging the external solution, another dialysis was conducted for two hours while stirring, thus obtaining a l-OHP-containing liposome preparation. The l-OHP-containing liposome preparation thus prepared had an average particle diameter of 185.2±14.9 nm (n=5).

In the Examples of the present invention, the average particle diameter of the liposome preparation was measured by a light scattering method using a NICOMP 370 HPL submicron particle analyzer (manufactured by Particle Sizing System, Inc.).

Example 2

HSPC (Hydrogenated Soy Phosphatidylcholine, Coatsome NC-21, manufactured by NOF Corporation), cholesterol (special grade, manufactured by Wako Pure Chemical Industries, Ltd.), and mPEG$_{2000}$-DSPE (1,2-distearoyl-sn-glycero-3-phosphoethanolamine-n-[methoxy(polyethylene glycol)-2000], Sunbright DSPE-020CN, manufactured by NOF Corporation) were dissolved in chloroform to obtain respective concentrations of 20 mM, 50 mM, and 5 mM. Subsequently, 5 mL of 20 mM HSPC solution, 1 mL of 50 mM cholesterol solution, and 2 mL of 5 mM mPEG$_{2000}$-DSPE solution were placed in a pear shaped flask. While reducing the pressure using an evaporator, the chloroform was removed to form a lipid thin film on the bottom of the pear shaped flask. The lipid thin films were dissolved in 6 ml of chloroform/diethyl ether (1:2 v/v). l-OHP was dissolved in a 5% glucose solution so that the concentration of l-OHP became 8 mg/mL. l-OHP solution thus prepared (2 mL) was added to the lipid solution and then mixed. The resulting mixture was sonicated at 35° C. for 15 minutes to form w/o emulsion, and the organic phase was removed under a reduced pressure using an evaporator for about one hour while being vortexed; the l-OHP was thereby encapsulated in liposome. Thereafter, the particle size was controlled and the non-capsulated pharmaceutical agent was removed in the same manner as in Example 1, obtaining a l-OHP liposome preparation. The l-OHP-containing liposome preparation thus prepared had an average particle diameter of 197.9±22.0 nm (n=5).

Example 3

A l-OHP-containing liposome preparation was produced in the same manner as in Example 1 except that PG-DSPE (Sunbright DSPE-PG10G, manufactured by NOF Corporation) was used instead of mPEG$_{2000}$-DSPE. The l-OHP-containing liposome preparation thus prepared had an average particle diameter of 130.4±48.3 nm (n=3).

Example 4

HSPC (Hydrogenated Soy Phosphatidylcholine, Coatsome NC-21, manufactured by NOF Corporation), cholesterol (special grade, manufactured by Wako Pure Chemical Industries, Ltd.), DC-6-14 (cationic lipid, O,O'-ditetradecanoyl-N-(alpha-trimethyl ammonio acetyl) diethanolamine chloride, manufactured by Sogo Pharmaceutical Co., Ltd.), and mPEG$_{2000}$-DSPE (1,2-distearoyl-sn-glycero-3-phosphoethanolamine-n-[methoxy(polyethylene glycol)-2000], Sunbright DSPE-020CN, manufactured by NOF Corporation) were dissolved in chloroform to obtain respective concentrations of 20 mM, 50 mM, and 5 mM. Subsequently, 5 mL of 20 mM HSPC chloroform solution, 1 mL of 50 mM cholesterol solution, and 2 mL of 5 mM DC-6-14 and 5 mM mPEG$_{2000}$-DSPE chloroform solution were placed in a pear shaped flask. While reducing the pressure using an evaporator, the chloroform was removed to form a lipid thin film on the bottom of the pear shaped flask. The lipid thin films were dissolved in 6 mL of chloroform/diethyl ether (1:2 v/v). l-OHP was dissolved in a 5% glucose solution so that the concentration of l-OHP became 8 mg/mL. l-OHP solution thus prepared (2 mL) was added to the lipid solution and then mixed. The resulting mixture was sonicated at 35° C. for 15 minutes, and the organic solvent was removed under a reduced pressure using an evaporator for about one hour while being vortexed; the l-OHP was thereby encapsulated in liposome. Thereafter, the particle size was controlled and the non-capsulated pharmaceutical agent was removed in the same manner as in Example 1, obtaining a l-OHP liposome preparation. The l-OHP-containing liposome preparation thus prepared had an average particle diameter of 202.4±14.7 nm (n=5).

Test Example 1

Formulation of Pharmaceutical Preparation

The l-OHP-containing liposome preparation obtained in Example 1 (hereunder referred to as DPPC liposome l-OHP) was used.

A l-OHP preparation (hereunder referred to as free l-OHP) was prepared by dissolving l-OHP in a 5% glucose solution.

A TS-1 preparation (hereunder referred to as TS-1) was prepared by dissolving the content encapsulated in a TS-1 capsule in water.

Antitumor Effect and Side Effects of Pharmaceutical Preparation Highly metastatic lung cancer cells, i.e., Lewis Lung carcinoma (LLC), were cultured in the presence of 5% $CO_2$ at 37° C. in a 10% FBS-DMEM. 0.1 mL of LLC cells containing $5 \times 10^6$ cells/mL were subcutaneously injected to the back of a male C57BL/6 mouse (5-week old, body weight of 20 g) to obtain a solid tumor-bearing mouse. It was confirmed that the tumor volume calculated by the following formula exceeded 50 mm$^3$ 6 days from the LLC cell infusion.

DPPC liposome l-OHP or free l-OHP was intravenously administered at the dose of 4.2 mg/kg as the l-OHP. TS-1 was orally administered at the dose of 6.9 mg/kg as tegafur. The DPPC liposome l-OHP and free l-OHP were administered at the 13$^{th}$ and 20$^{th}$ days post cell inoculation, and TS-1 was administered every day from 6 days post cell inoculation until the end of the experiment.

The tumor volume was calculated by the following formula from 6 days post cell inoculation. The antitumor effect was evaluated using the relative tumor volume ratio as an index.

$$\text{Tumor volume} = \tfrac{1}{2} \times a \times b^2$$

(a: major axis of the tumor site, b: minor axis of the tumor site)

Change in the mouse body weight was monitored as an index of side effects.

Figure 1:
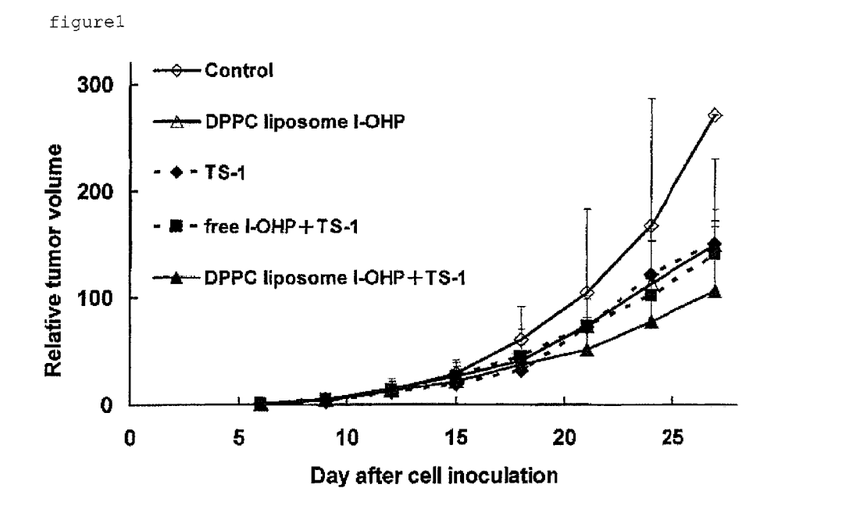
FIG. 1 is a graph showing the increases in relative tumor volumes in Test Example 1.
Figure 2:
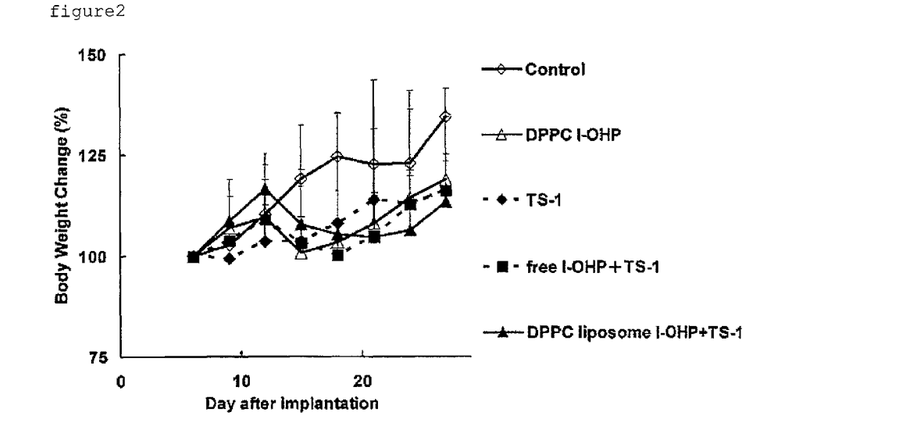
FIG. 2 is a graph showing changes in the body weight of mice in Test Example 1.

As is clear from the results shown in FIG. 1, combination therapy of DPPC liposome l-OHP and TS-1 showed higher antitumor effect than combination of free l-OHP and TS-1. However, the results shown in FIG. 2 indicate that there was no significant difference in the change in body weight between the combination of TS-1 with DPPC liposome l-OHP and with free l-OHP. A remarkable increase in toxicity was not observed.

Test Example 2

The antitumor effect and side effects were evaluated in the same manner as in Test Example 1 except that the l-OHP-containing liposome preparation obtained in Example 2 was used (hereunder referred to as HSPC liposome l-OHP).

Figure 3:
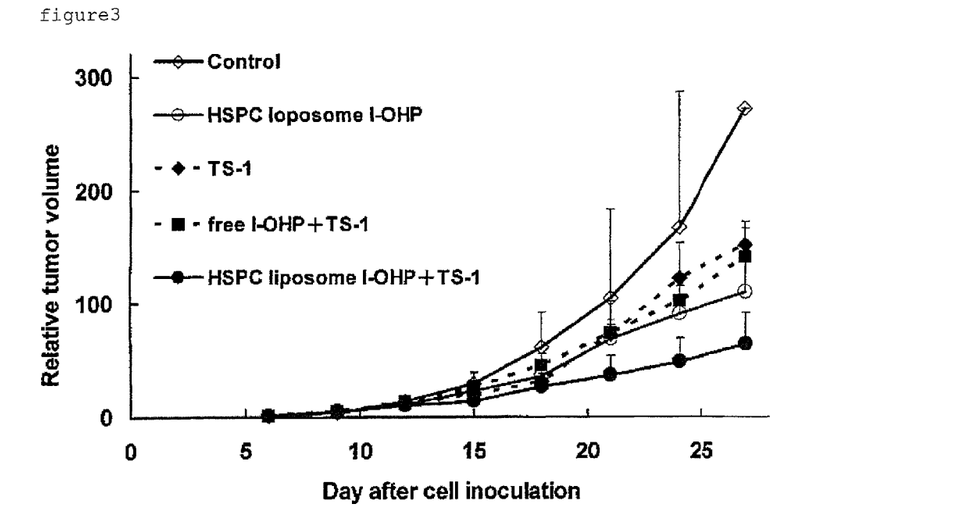
FIG. 3 is a graph showing increases in relative tumor volumes in Test Example 2.
Figure 4:
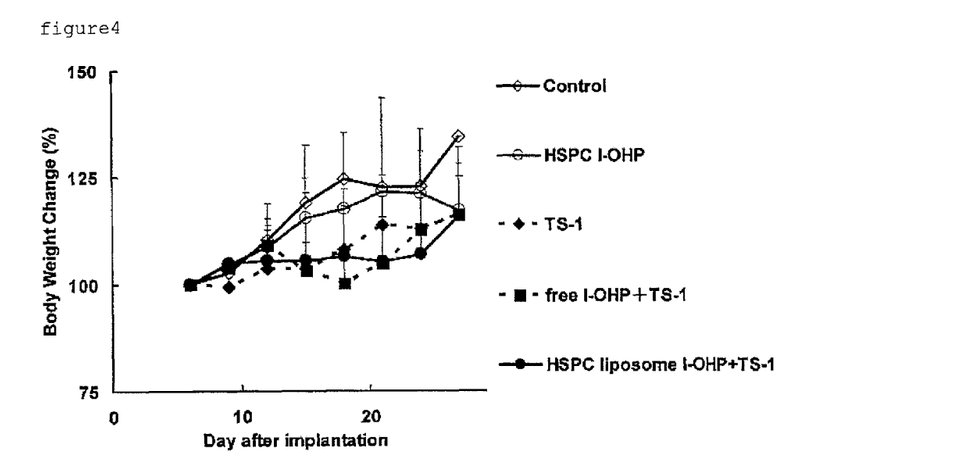
FIG. 4 is a graph showing changes in the body weight of mice in Test Example 2.

As is clear from the results shown in FIG. 3, combination therapy of HSPC liposome l-OHP with TS-1 showed a higher antitumor effect than combination of free l-OHP with TS-1. However, the results shown in FIG. 4 clearly indicate that there was no significant difference in the change in body weight between the combination of TS-1 with HSPC liposome l-OHP and with free l-OHP. A remarkable increase in toxicity was not observed.

Test Example 3

A pharmaceutical preparation was formulated in the same manner as in Test Example 1. The resulting pharmaceutical preparation was administered to a tumor-bearing mouse, and the number of survival days of the mouse was monitored.

Figure 5:
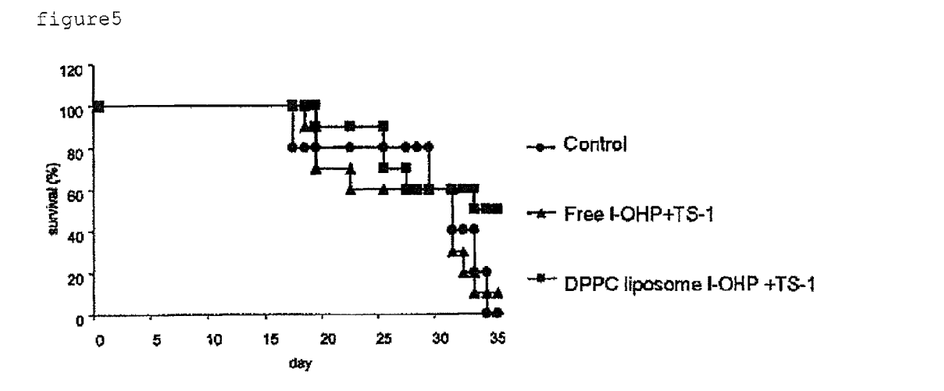
FIG. 5 is a graph showing the survival of mice in days after cell inoculation in Test Example 3.

As is clear from the results shown in FIG. 5, when TS-1 was administered in combination with DPPC liposome l-OHP, a survival rate was superior to the case of combination with free l-OHP.

Test Example 4

A pharmaceutical preparation was prepared in the same manner as in Test Example 2. The resulting pharmaceutical preparation was administered to a tumor-bearing mouse, and the survival days of the mouse were monitored.

Figure 6:
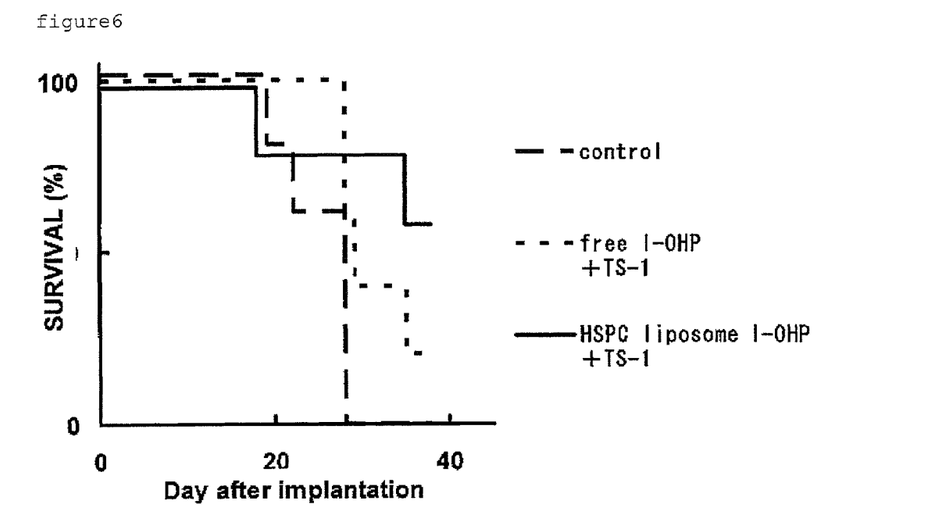
FIG. 6 is a graph showing the survival of mice in days after cell inoculation in Test Example 4.

As is clear from the results shown in FIG. 6, when TS-1 was administered in combination with HSPC liposome l-OHP, a survival rate was superior to the case of combination with free l-OHP.

Test Example 5

The antitumor effect was evaluated in the same manner as in Test Example 1 except that the l-OHP-containing liposome preparation obtained in Example 3 was used (hereunder referred to as PG10 liposome l-OHP).

Figure 7:
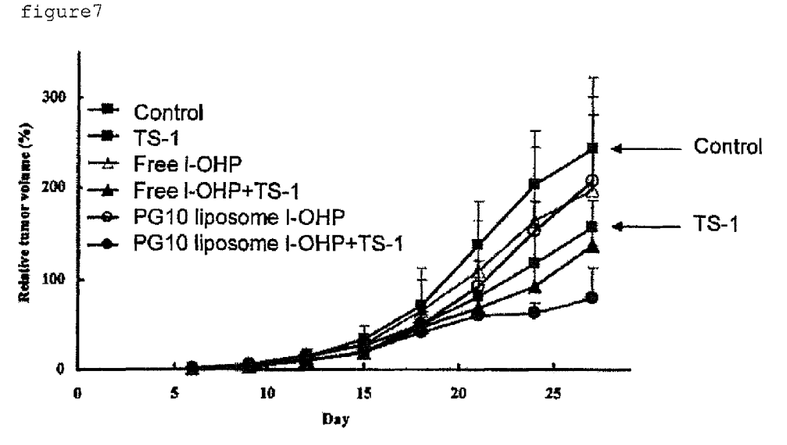
FIG. 7 is a graph showing increases in relative tumor volumes in Test Example 5.

As is clear from the results shown in FIG. 7, combination therapy of PG10 liposome l-OHP with TS-1 showed higher an antitumor effect than combination of free l-OHP with TS-1.

Test Example 6

Formulation of Pharmaceutical Preparation

A pharmaceutical preparation was formulated in the same manner as in Test Example 2.
Antitumor Effect and Side Effects of Pharmaceutical Preparation Mouse colon carcinoma cells, i.e., Colon 26, were cultured in the presence of 5% $CO_2$ at 37° C. in a 10% FBS-DMEM. 0.1 mL of Colon 26 cells containing $2\times10^7$ cells/mL were subcutaneously injected to the back of a male BALB/c mouse (5-week old, body weight of 20 g) to obtain a solid tumor-bearing mouse. It was confirmed that the tumor volume calculated by the following formula exceeded 50 $mm^3$ 7 days post the Colon 26 cells inoculation.

HSPC liposome l-OHP or free l-OHP was intravenously administered at the dose of 4.2 mg/kg as the l-OHP. TS-1 was orally administered at the dose of 6.9 mg/kg as tegafur. The HSPC liposome l-OHP and free l-OHP were administered at the $14^{th}$ and $21^{st}$ days post cell inoculation, and the TS-1 was administered every day from 7 days post cell inoculation until the end of the experiment.

Other antitumor effects and side effects were evaluated in the same manner as in Test Example 2.

Figure 8:
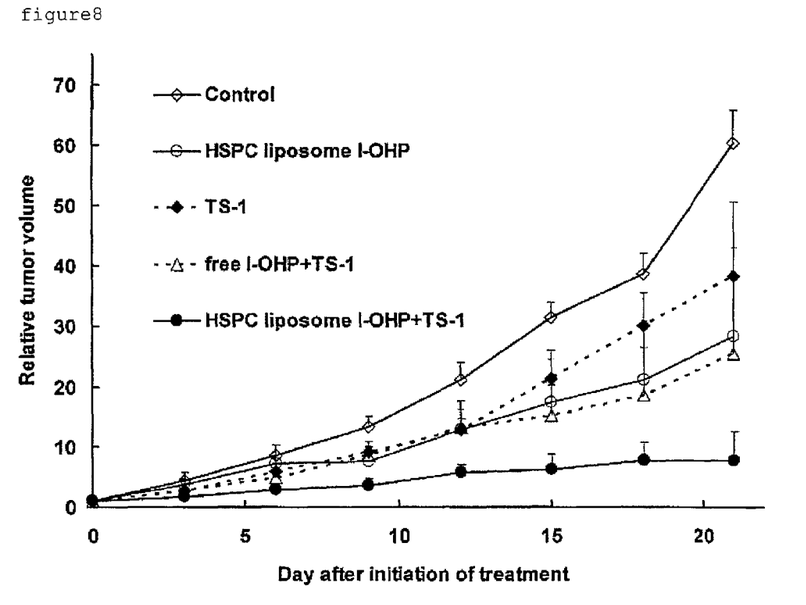
FIG. 8 is a graph showing increases in relative tumor volumes in Test Example 6.
Figure 9:
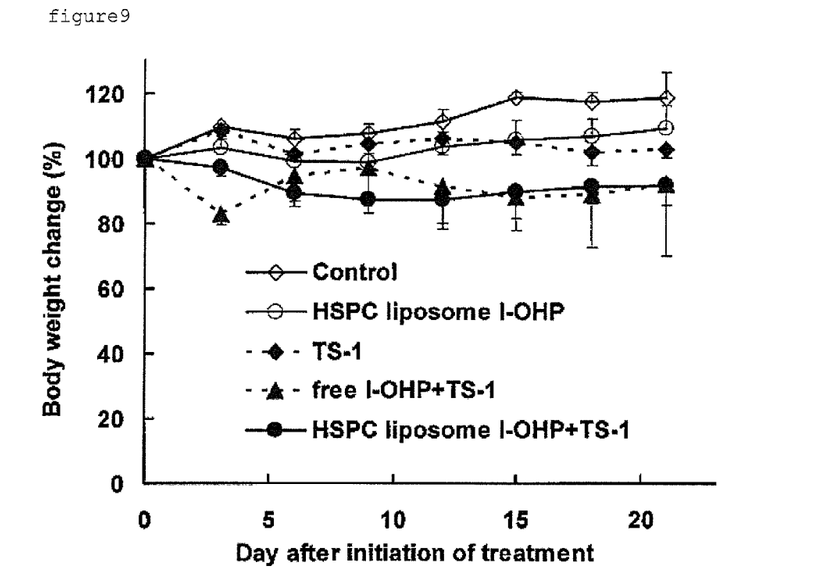
FIG. 9 is a graph showing changes in the body weight of mice in Test Example 6.

As is clear from the results shown in FIG. 8, an antitumor effect of combination therapy of HSPC liposome l-OHP plus TS-1 was superior to combination of free l-OHP plus TS-1. However, the results shown in FIG. 9 clearly indicated that there was no significant difference in the body weight changes between TS-1 treatment in combination with HSPC liposome l-OHP and with free l-OHP. In other words, a remarkable increase in toxicity was not observed.

Test Example 7

A pharmaceutical preparation was formulated in the same manner as in Test Example 6. The resulting pharmaceutical preparation was administered to a tumor-bearing mouse, and the number of survival days of the mouse was monitored.

Figure 10:
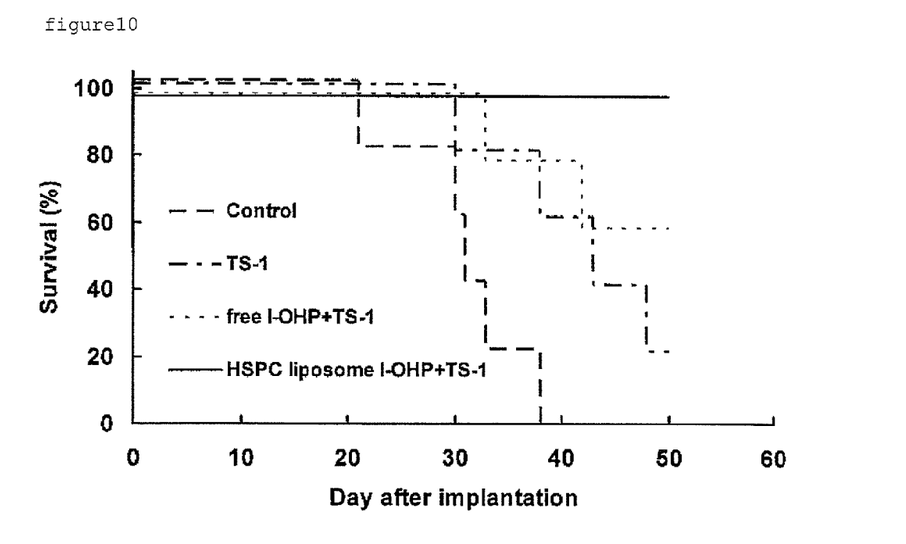
FIG. 10 is a graph showing the survival of mice in days after cell inoculation in Test Example 7.

As is clear from the results shown in FIG. 10, combination therapy of HSPC liposome l-OHP plus TS-1 showed prolonged survival rate compared with combination of free l-OHP plus TS-1.

The results presented above suggest that by encapsulating l-OHP in a liposome, i.e., a l-OHP containing liposome preparation, the antitumor effect and survival rate of l-OHP containing liposome can be remarkably increased when combined with TS-1, while the toxicity level is almost the same as the case where l-OHP is administered in combination with TS-1. The increase in antitumor activity is probably attributed to an improved biodistribution and enhanced tumor localization of l-OHP as a result of its optimum liposomalization.

The present invention revealed that, by encapsulation of l-OHP into a liposome preparation, the antitumor activity of the combination therapy of l-OHP plus a combination drug containing tegafur, gimeracil and oteracil potassium, can be enhanced, and the toxicity attributed to liposomalization of l-OHP is not found. This indicated that the combination therapy using l-OHP liposome preparation with a combination drug containing tegafur, gimeracil and oteracil potassium is suggested to be a promising cancer treatment.

The invention claimed is:

1. An antitumor agent combinedly comprising a liposome preparation obtainable by encapsulating oxaliplatin in a liposome, and a combination drug containing tegafur, gimeracil and oteracil potassium, wherein the liposome consists of dipalmitoylphosphatidylcholine, cholesterol and 1,2-distearoyl-sn-glycero-3-phosphoethanolamine-n-[methoxy (polyethylene glycol)-2000]; hydrogenated soy phosphatidylcholine, cholesterol and 1,2-distearoyl-sn-glycero-3-phosphoethanolamine-n-[methoxy(polyethylene glycol)-2000]; or dipalmitoylphosphatidylcholine, cholesterol and 1,2-distearoyl-sn-glycero-3-phosphoethanolamine-polyglycerin,
 the oxaliplatin is used in a proportion of 0.1 to 5 mol per 1 mol of tegafur, and
 the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

2. The antitumor agent according to claim 1, wherein the liposome preparation is administered intravenously, intraperitoneally, intramuscularly or subcutaneously, and the combination drug containing tegafur, gimeracil and oteracil potassium is administered orally.

3. An antitumor effect potentiator, which is a liposome preparation containing an effective amount of oxaliplatin in a liposome, for enhancing antitumor activity of a therapeutically effective amount of a combination drug containing tegafur, gimeracil and oteracil potassium, wherein said liposome consists of dipalmitoylphosphatidylcholine, cholesterol and 1,2-distearoyl-sn-glycero-3-phosphoethanolamine-n-[methoxy(polyethylene glycol)-2000]; hydrogenated soy phosphatidylcholine, cholesterol and 1,2-distearoyl-sn-glycero-3-phosphoethanolamine-n-[methoxy(polyethylene glycol)-2000]; or dipalmitoylphosphatidylcholine, cholesterol and 1,2-distearoyl-sn-glycero-3-phosphoethanolamine-polyglycerin, the oxaliplatin is used in a proportion of 0.1 to 5 mol per 1 mol of tegafur, and the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

4. A method for treating cancer comprising administering a liposome preparation which contains oxaliplatin encapsulated in a liposome, and a combination drug containing tegafur, gimeracil and oteracil potassium to a cancer patient, at an effective dose, respectively, wherein the liposome consists of dipalmitoylphosphatidylcholine, cholesterol and 1,2-distearoyl-sn-glycero-3-phosphoethanolamine-n-[methoxy(polyethylene glycol)-2000]; hydrogenated soy phosphatidylcholine, cholesterol and 1,2-distearoyl-sn-glycero-3-phosphoethanolamine-n-[methoxy(polyethylene glycol)-2000]; or dipalmitoylphosphatidylcholine, cholesterol and 1,2-distearoyl-sn-glycero-3-phosphoethanolamine-polyglycerin, the cancer to be treated is at least one selected from the group consisting of colon cancer, and lung cancer, the oxaliplatin is used in a proportion of 0.1 to 5 mol per 1 mol of tegafur, and the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

5. A method for enhancing the antitumor activity of a therapeutically effective amount of a combination drug containing tegafur, gimeracil and oteracil potassium, comprising administering a liposome preparation which contains oxaliplatin encapsulated in a liposome to a cancer patient, wherein the liposome consists of dipalmitoylphosphatidylcholine, cholesterol and 1,2-distearoyl-sn-glycero-3-phosphoethanolamine-n-[methoxy(polyethylene glycol)-2000]; hydrogenated soy phosphatidylcholine, cholesterol and 1,2-distearoyl-sn-glycero-3-phosphoethanolamine-n-[methoxy(polyethylene glycol)-2000]; or dipalmitoylphosphatidylcholine, cholesterol and 1,2-distearoyl-sn-glycero-3-phosphoethanolamine-polyglycerin, the cancer to be treated is at least one selected from the group consisting of colon cancer, and lung cancer, the oxaliplatin is used in a proportion of 0.1 to 5 mol per 1 mol of tegafur, and the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

6. A kit comprising a liposome preparation obtainable by encapsulating oxaliplatin in a liposome, and a combination drug containing tegafur, gimeracil and oteracil potassium wherein the liposome consists of dipalmitoylphosphatidylcholine, cholesterol and 1,2-distearoyl-sn-glycero-3-phosphoethanolamine-n-[methoxy(polyethylene glycol)-2000]; hydrogenated soy phosphatidylcholine, cholesterol and 1,2-distearoyl-sn-glycero-3-phosphoethanolamine-n-[methoxy(polyethylene glycol)-2000]; or dipalmitoylphosphatidylcholine, cholesterol and 1,2-distearoyl-sn-glycero-3-phosphoethanolamine-polyglycerin, the oxaliplatin is used in a proportion of 0.1 to 5 mol per 1 mol of tegafur, and the gimeracil is used in a proportion of 0.1 to 5 mol per 1 mol of tegafur, and the oteracil potassium is used in a proportion of 0.1 to 5 mol per 1 mol of tegafur in the combination drug containing tegafur, gimeracil and oteracil potassium.

\* \* \* \* \*